United States Patent [19]
Horas et al.

[11] Patent Number: 6,056,755
[45] Date of Patent: May 2, 2000

[54] METHOD FOR TRANSPORTING A BONE SEGMENT IN ORDER TO BRIDGE A BONE DEFECT AND DEVICE FOR CARRYING OUT THE METHOD

[76] Inventors: Uwe Peter Horas, Neumannstrasse 76, Frankfurt 60433, Germany; Marcus Erben, Hölderlinring 10A, Hattersheim 65795, Germany

[21] Appl. No.: 09/180,266
[22] PCT Filed: May 9, 1997
[86] PCT No.: PCT/EP97/02370
  § 371 Date: Jan. 18, 1999
  § 102(e) Date: Jan. 18, 1999
[87] PCT Pub. No.: WO97/42896
  PCT Pub. Date: Nov. 20, 1997

[30] Foreign Application Priority Data

May 9, 1996 [DE] Germany ............................ 196 18 552

[51] Int. Cl.[7] .................................................. A61F 5/00
[52] U.S. Cl. .................. 606/86; 606/62; 606/63
[58] Field of Search ................. 606/86, 88, 90, 606/101, 105, 62–70, 57–61; 623/20, 21, 22, 17, 28, 23, 29

[56] References Cited

U.S. PATENT DOCUMENTS

| | | | |
|---|---|---|---|
| 4,862,883 | 9/1989 | Freeland | 128/92 |
| 5,356,411 | 10/1994 | Spievack | 606/63 |
| 5,505,733 | 4/1996 | Justin et al. | 606/63 |
| 5,855,579 | 1/1999 | James et al. | 606/62 |

*Primary Examiner*—Michael Buiz
*Assistant Examiner*—Lien Ngo
*Attorney, Agent, or Firm*—Cohen, Pontani, Lieberman & Pavane

[57] ABSTRACT

In order to transport a bone segment (5) in order to bridge a bone defect (4) on a tubular bone (1) in a self-inductive manner using a fully implanted device, it is proposed for the segment (5) to be driven by means of a tensile force which is generated in the cord (10) or the like by means of flexural movement of the healthy bone (9) which is articulated to the joint (8) the tensile force, from said cord or the like, is directly or indirectly applied to the segment (5) through the medullary nail in an intramedullary fashion.

16 Claims, 2 Drawing Sheets

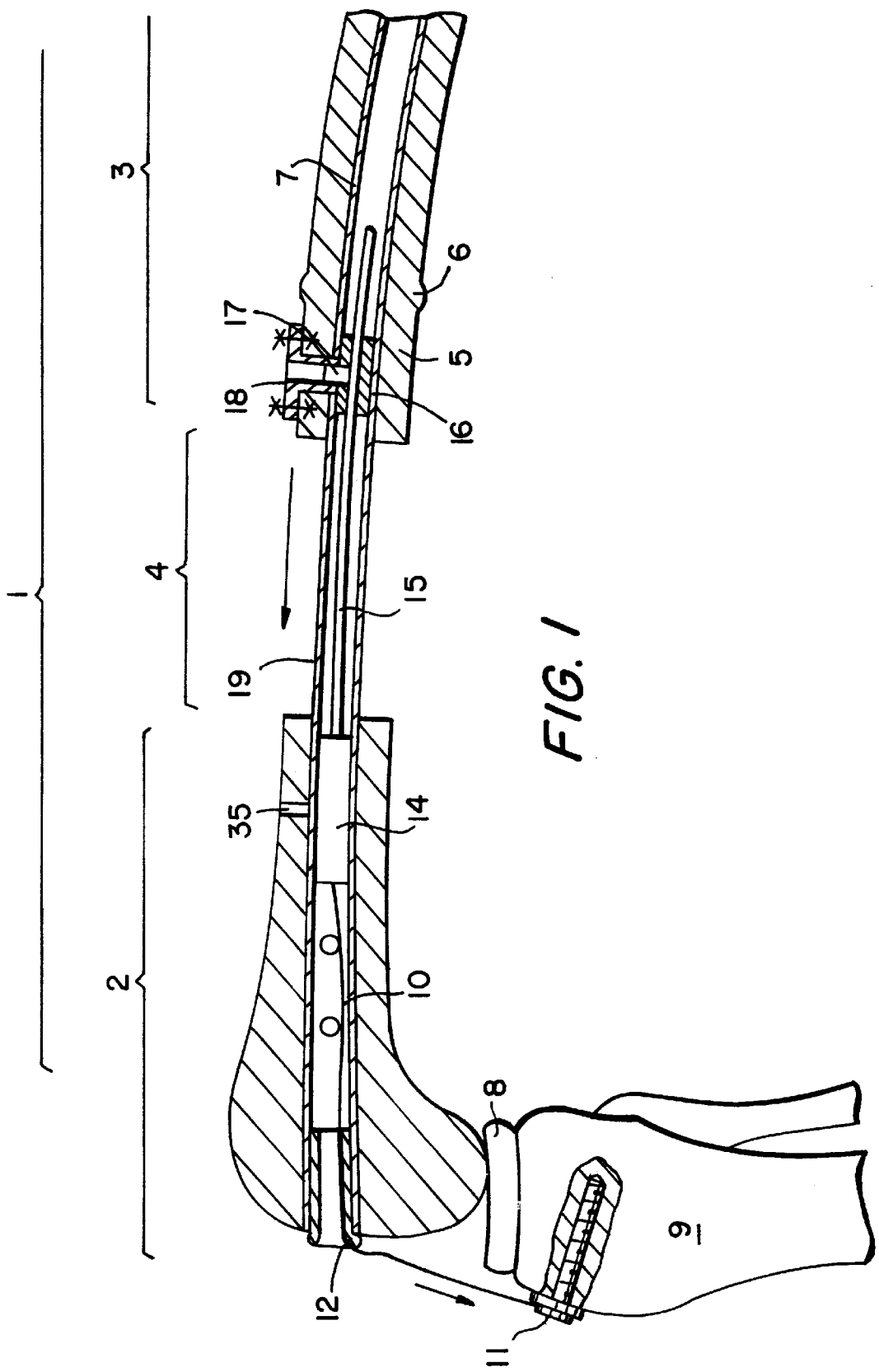
FIG. I

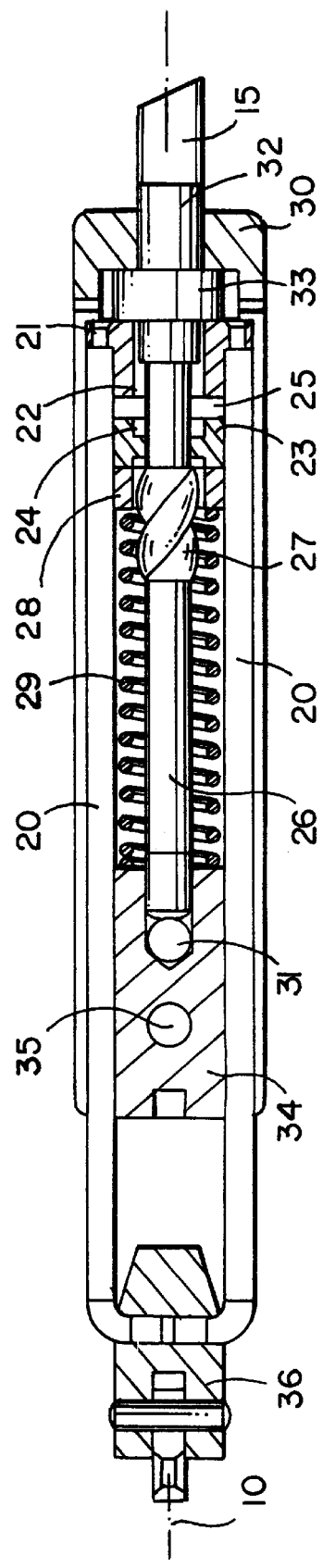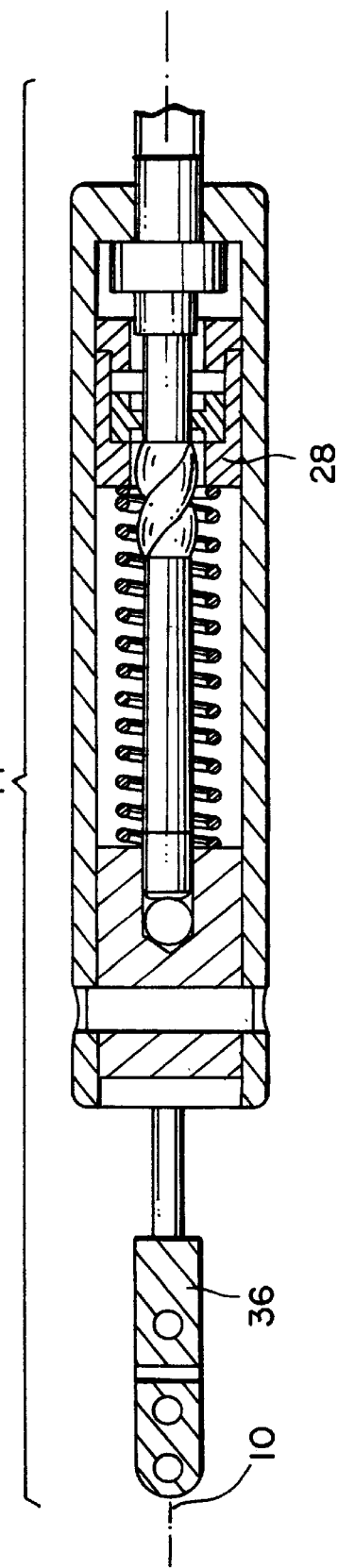

METHOD FOR TRANSPORTING A BONE SEGMENT IN ORDER TO BRIDGE A BONE DEFECT AND DEVICE FOR CARRYING OUT THE METHOD

BACKGROUND OF THE INVENTION

1. Field of the Invention

The invention relates to a method of the generic type described in the preamble of claim 1.

2. Description of Related Art

In accident surgery and orthopedic practice, it is often necessary to bridge bone defects on long tubular bones. Such operations involve the creation of new bone tissue by displacing a preserved bone segment along the long tubular bone, essentially by means of the osteogenic power of the periosteum.

Segment displacement is a tried and tested method which has been known for a long time. Currently, the force required to transport the segment is generally produced extracorporeally by means of so-called Fixateur externe systems (external tensioners) or, using the most recent developments, in a fully implanted manner by means of an electric motor which is positioned intracorporeally and an intramedullary implant (medullary nail). A further method uses a rotational principle (tube inside tube) in conjunction with a ratchet in order to introduce its force, but this method can only be used to extend tubular bones. All of the known techniques to date have drawbacks, some of which are considerable, for the patient, such as the risk of infection when external tensioners are used, uncomfortable handling and long periods of inpatient treatment.

Furthermore, as in the case of the implant with an electric motor which cannot be re-used, disproportionately high cost are incurred.

SUMMARY OF THE INVENTION

The object of the invention is to develop an alternative method for transporting a bone segment with devices and which are fully implanted, which can be self operated, i.e. without external aid, by the patient him/herself and avoids the drawbacks mentioned above.

The object is achieved by means of a method as described in the defining part of claim 1. The fundamental novelty of the method according to the invention is the inclusion of the joint adjoining the damaged tubular bone. To drive the bone segment, the method uses the tensile force which is generated during the flexural movement of the two bones which are articulated at the joint and which is converted into a translational movement of a traction cord which engages on the healthy bone, spans the condyles and the joint outside the joint pivot point, is guided inside the medullary nail in the medullary cavity of the defective bone and acts directly or indirectly on the segment which is to be moved. The cord can be tensioned in a self-inductive manner by the patient. There is no need for any external power source, and a simple, inexpensive device is sufficient. The patient can control the procedure without help from a physician. Passive movement is also possible if the patient is unable to carry out the active movement him/herself.

The device is fully implanted and does not include any extracorporeal components. The method may be used at the knee joint and at the elbow joint. A precondition for its use is that there be sufficient joint mobility with regard to flexion/extension.

A drive which directly transmits the tensile force from the bent healthy bone of the joint to the segment and converts the translational movement of the traction cord into an axial displacement of the segment is proposed as a further development of the method according to the invention.

A device for carrying out the method according to the invention has a traction cord or similar traction element, bone end of the traction cord can be attached to the healthy bone of the joint by means of an anchor and the other end can be connected to the bone segment in such a manner that it is possible, by means of a flexural movement of the healthy bone relative to the defective bone, to transmit a tensile force and a translational movement from the anchor to the bone segment.

BRIEF DESCRIPTION OF THE DRAWINGS

Further details of the invention can be found in the appended drawings, in which:

FIG. 1 shows a section through a device according to the invention, along the longitudinal axis of the bone, based on the example of a defective femur.

FIGS. 2 and 3 show two sections, rotated through 90°, through a drive according to the invention, along the longitudinal axis of the medullary nail.

DETAILED DESCRIPTION OF THE PREFERRED EMBODIMENTS

In the example in accordance with FIG. 1, the preserved proximal and distal parts 3 and 2 respectively of a defective femur 1 are supported by a medullary nail 7 which has been driven into the medullary cavity and are held in position with respect to one another, spaced apart by the distance of the defect 4. A preserved bone segment 5 undergoes osteotomy from the proximal part 3 (i.e. it is cleaved off using a chisel while retaining the periosteum) and is to be transported toward the distal bone part 2 in order to bridge the defect 4. If the speed at which the segment 5 is transported is set to be appropriate for growth, the callus 6 fills the constantly widening space between segment 5 and proximal bone part 3 with newly formed bone tissue, so that at the end of the transportation of the segment 5 the defect 4 is bridged. For transport purposes, the segment 5 is suitably connected to a drive 14, and is preferably screwed onto a spindle nut 16 via a bone sleeve 18, by means of a segment screw 17. The screw thread of a threaded rod 15 is screwed into the spindle nut 16. The spindle 15 can be driven by a drive 14, i.e. is rotated, and by means of its rotation in the nut 16 transports the segment 5 along the medullary nail 7 in order for it to be connected to the distal bone part 2, the segment 5 is guided by the screw 17 into a slot 19 in the medullary nail 7. In the present example, the threaded rod is connecting the segment 5 and the drive 14 runs inside the medullary nail 7. In this case, the drive 14 ensures that when the joint is flexed in order to excite the osteogenic activity of the periosteum, the required, anatomically optimized tension direction and the tensile force which is biologically optimized in terms of time are exerted on the segment 5. Drive 14 is anchored to bone part 2 and thereby medullary nail 7 via an anchor screw connection 35.

In the joint 8, in the present example the knee joint, the defective femur 1 and the healthy tibia 9 are pivotally connected to one another. A traction cord 10 is attached to the condyle of the healthy bone 9 in an anchor 11. From the anchor 11, the traction cord 10 is introduced, in such a manner that it exerts an eccentric tensile force, into the drive with respect to the anatomical-physiological pivot point of the joint 8, on the extension side, along the joint 8, through the rounded mouth of a bushing 12, which is fitted into the joint-side end of the bone part 2, and a passage in the adjoining medullary nail 7. Pivoting the healthy bone 9 about the joint pivot point in the anticlockwise direction relative to the defective bone 1 pulls the traction cord 10 out of the medullary nail 7 in the direction of the arrow and generates a codirectional translational cord movement and tensile force. Cord movement and tensile force are converted, by means of a suitable drive 14, into an axial displacement of the segment, so that the segment 5 is transported in the direction of the bone part 2, with the result that the defect is closed up toward the bone part 2. In the design illustrated, the cord movement and the tensile force are converted, in a drive 14 which acts in a similar way to a mechanically driven gyroscope, into a rotational movement of the threaded rod 15 which transports the nut 16 and therefore the segment 5 toward the bone part An exemplary embodiment of such a drive 14 is illustrated in FIGS. 2 and 3. The drive 14 has a cylindrical housing 30 in which a spindle 26 is mounted by means of a rear bearing 31 supported by spring support 34, which can be removed for assembly purposes and is fixed in the housing 30 by the bolt 35, and a front bearing 32 and is secured from axial displacement by a collar 33. A front coupling part half 21, a rear coupling part half 23, a sleeve 28 and a coil spring 29 are arranged movably and rotatably on the spindle 26, in the above order as seen from the front (that end of the drive 14 which is remote from the joint 8) toward the rear. The tensile force acting in the direction toward the joint 8 and the translational movement from the traction cord 10 are introduced into the drive 14 in a connection element 36. Traction rods 20 transmit the translational movement to the front coupling half 21. They are pulled back by a distance 25 between the coupling halves 21 and 23 and are pressed onto the rear coupling half 23, causing teeth 22 and 24, arranged on the two coupling halves 21 and 23, respectively; engage each other. The coupling half 23 of the coupling simultaneously forms the nut for the screw thread 27 on the spindle 26. The characteristic of the screw thread 27 is selected in such a way that when the cord tension begins to act, the nut can easily be pushed onto the screw thread 27 of the spindle 26, thus causing the spindle 26 to rotate, and this rotation can then be transmitted, via threaded rod 15, to the nut 16 on the segment 5, thereby transporting the segment along the defect 4.

The length of the screw thread 27 of the spindle 26 is dependent on the thread pitch selected. As a result, the length of the screw thread 27 is determined by the fact that the number of spindle revolutions in the nut 16 which it produces during the translational movement of the coupling half 23 produces a limited transport distance for the segment 5 which is determined in accordance with medical requirements, e.g. 1 mm. It is necessary for the screw threads of spindle 26 and nut 16 to be accurately adapted to one another in order to achieve the desired transport distance.

The cup-like sleeve 28 can be rotated freely and is turned inside out, without a connection, over the coupling part 23 acting as the nut sleeve 28 is moved backward, together with the coupling half 21, by the traction rods 20 and thus stresses the compression spring 29. To achieve the required transport distance for the segment 5 or the rotations in the nut 16 which are necessary for this purpose, the rear coupling half 23 (which is the nut for the spindle thread 27) has to be moved backward completely, i.e. at least as far as behind the screw thread 27 on the spindle 26. Moving the nut back further has no effect, since the spindle 26 does not have a screw thread in that area. This part of the spindle 26 forms the play for the traction path of the cord 10 and is used to compensate for (buffer) an uncontrolled cord traction, which is inevitable in the joint 8 when the patient moves the joint without any control. When the tension in the traction cord 10 ends, the spring 29, via the sleeve 28, presses the coupling half 21 and—after the coupling half 23 has been decoupled—the latter also back into the starting position. During the restoring movement carried out by means of the spring pressure, a suitable design of the sleeve 20 means that firstly the front coupling part 21 is pressed away to the distance 25 and, as a result, the coupling part 23 and the spindle 26 are decoupled.

The drive 14 is then ready to transport the segment 5 again.

What is claimed is:

1. A method for transporting a preserved bone segment for bridging a bone defect on a bone adjoining a knee or elbow joint, the bone defect being between a first and second bone parts being supported and maintained at a distance from each other by a medullary nail, the method comprising the steps of:

connecting the preserved bone segment to the second bone part remote from the joint using a callus;

displacing the preserved bone segment toward the first bone part closer to the joint; and closing the defect by utilizing osteogenic power of a periosteum;

wherein said step of displacing comprises the step of self-inductively transporting the preserved bone segment by generating a tensile force in response to flexural movement of a healthy bone articulated at the joint and applying the tensile force to the preserved bone segment.

2. The method according to claim 1, wherein said step of applying a tensile force further comprises the step of providing a traction element having one end attached to the healthy bone and an opposite end connected to the bone segment.

3. The method according to claim 2, further comprising the step of guiding the traction cord through the medullary nail in an intramedullary manner.

4. The method according to claim 2, further comprising the step of providing a drive connected at one end to the opposite end of said traction cord and connected at an opposing end to the bone segment for converting a tensile movement of the traction cord into an axial displacement of the drive which causes the longitudinal displacement of the bone segment.

5. The method according to claim 4, further comprising the steps of:

providing an elongated threaded rod having one end coupled to said drive, and an opposing end;

providing a nut within said preserved bone segment for receiving said opposing end of said threaded rod;

converting the tensile movement of the traction cord into rotational movement of the threaded rod, said rotational movement interacting with said nut to effect the longitudinal displacement of said preserved bone segment.

6. The method according to claim 2 further comprising the steps of:

providing an anchor in the healthy bone for attaching element to the healthy bone; and eccentrically articulating the traction element on an extension side along the joint to the defective bone as far as the bone segment with respect to an anatomical-physiological pivot point of the joint.

7. The method according to claim 3, wherein said step of guiding guides the traction element to the bone segment through a longitudinal passage in the medullary nail and further comprises the step of providing a bushing in a joint side of the first bone part.

8. The method according to claim 4, further comprising the step of anchoring the drive in the first bone part.

9. A device for transporting a preserved bone segment for bridging a bone defect on a bone adjoining a knee or elbow joint, the bone defect being between a first and second bone part being supported and maintained at a distance from each other by a medullary nail, the device comprising:

a traction element having one end adopted to be attached to a healthy bone and an opposing end adopted to be connected to the preserved bone segment such that flexural movement of the healthy bone relative to the defective bone transmits a tensile force and a translational movement from the point of connection to the healthy bone to the preserved bone segment; and an anchor for attaching to the healthy bone for coupling said traction element to the healthy bone.

10. The device according to claim 9, wherein said traction element is operably guided through the medullary nail in an intramedullary fashion.

11. The device according to claim 9, further comprising a drive disposed within the first bone part and connected at one end to said traction element, said drive having a threaded rod extending through said medullary nail and into said second bone part such that tensile movement of said traction element produces a force on said preserved bone segment via the threaded rod in a direction toward the first bone part to close the bone defect.

12. The device according to claim 11, further comprising a bushing mounted in a joint side end of the first bone part, said traction element being guided along said bushing into a longitudinal passage of the medullary nail and being connected to said drive.

13. The device according to claim 11, further comprising anchor means for securing said drive within said first bone part.

14. The device according to claim 11, further comprising means for connecting the preserved bone segment to said drive via said threaded rod, said means for connecting comprising:

a bone sleeve disposed in the preserved bone segment;

a nut threadably engaging said threaded rod; and a segment screw for securing said preserved bone segment to said nut.

15. The device according to claim 14, wherein said medullary nail comprises a slot extending across the bone defect, said nut together with said segment screw being guided in said slot during operable displacement of said bone segment.

16. The device according to claim 11, wherein said drive further comprises:

a cylindrical housing fixed within the medullary nail in a region of the first bone part and having a front bearing and a removable rear bearing;

a spindle rotatably mounted within said housing and having a longitudinal axis on which said spindle is not displaceable, and an internal threaded part, said threaded rod being integrally formed with said spindle rod and extending out of said housing through a said front bearing for driving a spindle nut;

a coupling having a front coupling part and a rear coupling part, said rear coupling part being shifted a distance on said spindle when in a decoupled position, said rear coupling part simultaneously being a nut for receiving said screw thread of said spindle;

a sleeve having walls slidably disposed over said coupling part and a sleeve edge pressing against said front coupling part;

a return spring having one side supported against said housing and an opposing side supported against said sleeve;

a connection element for connection to said traction element; and traction rods acting on said connection element and being guided into said housing to transmit the translational movement of said traction element to said front coupling part;

wherein said coupling, sleeve, return spring, connection element and traction rods are displaceably and rotatably disposed on said spindle.

* * * * *